United States Patent
Hooper et al.

(10) Patent No.: US 8,800,066 B2
(45) Date of Patent: Aug. 12, 2014

(54) FOG-RESISTANT GOGGLES

(75) Inventors: Bryan Hooper, Brea, CA (US); James C. Wang, Walnut, CA (US)

(73) Assignee: I.E. Manufacturing LLC, Ontario (CA)

( * ) Notice: Subject to any disclaimer, the term of this patent is extended or adjusted under 35 U.S.C. 154(b) by 675 days.

(21) Appl. No.: 11/832,281

(22) Filed: Aug. 1, 2007

(65) Prior Publication Data

US 2008/0047050 A1 Feb. 28, 2008

Related U.S. Application Data

(60) Provisional application No. 60/835,458, filed on Aug. 4, 2006.

(51) Int. Cl.
*A61F 9/02* (2006.01)

(52) U.S. Cl.
USPC .................................................. 2/435

(58) Field of Classification Search
USPC ...................................... 2/435–437
See application file for complete search history.

(56) References Cited

U.S. PATENT DOCUMENTS

| | | | | |
|---|---|---|---|---|
| 4,264,988 A * | 5/1981 | Specht | | 2/431 |
| 5,617,588 A * | 4/1997 | Canavan et al. | | 2/428 |
| 5,867,841 A * | 2/1999 | Chiang | | 2/436 |
| 6,138,285 A | 10/2000 | Robrahn et al. | | |
| 6,138,286 A * | 10/2000 | Robrahn et al. | | 2/436 |
| D456,037 S | 4/2002 | Tabacchi | | |
| 6,665,885 B2 * | 12/2003 | Masumoto | | 2/436 |
| 6,732,382 B2 * | 5/2004 | Dondero | | 2/436 |
| 6,772,448 B1 * | 8/2004 | Hockaday et al. | | 2/435 |
| 7,137,153 B2 * | 11/2006 | Hussey | | 2/437 |
| D542,829 S | 5/2007 | Hsu | | |
| D549,267 S | 8/2007 | Chen et al. | | |
| D551,278 S | 9/2007 | Moritz et al. | | |
| D551,279 S | 9/2007 | Chen | | |
| D551,280 S | 9/2007 | Li | | |
| D556,238 S | 11/2007 | Yang | | |
| D556,811 S | 12/2007 | Bruck | | |
| D559,299 S | 1/2008 | Tabacchi | | |
| D577,054 S | 9/2008 | Moritz | | |
| D581,964 S | 12/2008 | Hooper et al. | | |
| D584,329 S | 1/2009 | Egger | | |
| 2002/0023292 A1 | 2/2002 | Masumoto | | |
| 2004/0103469 A1 | 6/2004 | Hussey | | |
| 2005/0015862 A1 | 1/2005 | Dondero | | |
| 2007/0033716 A1 | 2/2007 | Dondero | | |
| 2008/0047050 A1 | 2/2008 | Hooper et al. | | |

FOREIGN PATENT DOCUMENTS

| | | |
|---|---|---|
| WO | WO 02/30227 | 4/2002 |
| WO | WO 2005/043980 | 5/2005 |

OTHER PUBLICATIONS

U.S. Appl. No. 29/328,666, filed Nov. 28, 2008, Hooper, et al.
Examination Report issued in Aug. 6, 2010, in New Zealand Patent Application No. 574600.
Office Action issued Dec. 4, 2013, in Canadian Patent Application No. 2,661,773.

* cited by examiner

*Primary Examiner* — Katherine Moran
(74) *Attorney, Agent, or Firm* — Oblon, Spivak, McClelland, Maier & Neustadt, L.L.P.

(57) ABSTRACT

The invention relates to fog-resistant goggles as well as to methods of defogging goggles during use and methods of producing fog-resistant goggles. Also included is a method and apparatus to direct airflow toward the lens and away from the eyes of an individual wearing the goggles.

18 Claims, 5 Drawing Sheets

FOG-RESISTANT GOGGLES

FIELD OF THE INVENTION

The present invention generally relates to fog-resistant goggles comprising at least one lens encompassed within a frame comprising a bottom portion and a top portion, wherein the top portion of the frame comprises at least one vent and wherein the bottom portion of the frame comprises at least one air flow channel which directs air toward the lens during use in an amount sufficient to reduce fogging as well as to methods of producing such goggles and to methods of defogging goggles. Such goggles possess improved properties and characteristics such as, for example, defogging the goggle lens during use while, at the same time, protecting the user's eyes from damaging or harmful airflow.

DISCUSSION OF THE BACKGROUND

The lens in a goggle (primarily a sports goggle such as ski- or snow-boarding goggles) has a strong tendency to accumulate condensation (fog) on the inside of the lens during use and activity. Without enough air circulation, the fog will not clear and will impair the user's ability to see during use.

The air flow in a standard sports goggle is uncontrolled. It typically starts at the bottom (bottom vent), fills the inner goggle space (area between the face and the lens), and exits from the top (top vent) once enough air has entered through bottom vent to create ventilation.

Such an uncontrolled airflow system has drawbacks. For example, the uncontrolled air flows into the user's eyes, often causing the eyes to dry, tear up, or develop some other condition, all of which can adversely affect sight during use. Given that goggles are often worn by users traveling at great speed, such problems affecting eyesight can be extremely dangerous. Thus, there remains a need in the art for safe, fog-resistant goggles.

Accordingly, one aspect of the present invention is a goggle which is able to reduce the amount of fog on the lens while, at the same time, able to address or overcome the aforementioned problems with prior art goggles.

SUMMARY OF THE INVENTION

The present invention relates to goggles comprising at least one lens encompassed within a frame comprising a bottom portion and a top portion, wherein the top portion of the frame comprises at least one vent and wherein the bottom portion of the frame comprises at least one air flow channel which directs air toward the lens during use in an amount sufficient to reduce fogging, preferably in an amount sufficient to substantially eliminate fogging.

The present invention further relates to molds for producing goggles comprising at least one lens encompassed within a frame comprising a bottom portion and a top portion, wherein the top portion of the frame comprises at least one vent and wherein the bottom portion of the frame comprises at least one air flow channel which directs air toward the lens during use in an amount sufficient to reduce fogging, preferably in an amount sufficient to substantially eliminate fogging.

The present invention also relates to processes, preferably injection molding processes, for producing goggles comprising at least one lens encompassed within a frame comprising a bottom portion and a top portion, wherein the top portion of the frame comprises at least one vent and wherein the bottom portion of the frame comprises at least one air flow channel which directs air toward the lens during use in an amount sufficient to reduce fogging, preferably in an amount sufficient to substantially eliminate fogging, comprising using the above-referenced mold.

The present invention further relates to methods for defogging goggles during use comprising directing air toward the lens in an amount sufficient to reduce fogging, preferably in an amount sufficient to substantially eliminate fogging.

The present invention also relates to methods for producing goggles comprising at least one lens encompassed within a frame comprising a bottom portion and a top portion, the method comprising adding at least one air flow insert comprising at least one air flow channel to the bottom portion of the frame so that the air flow channel directs air toward the lens during use in an amount sufficient to reduce fogging, preferably in an amount sufficient to substantially eliminate fogging.

The present invention further relates to methods for producing goggles comprising at least one lens encompassed within a frame comprising a bottom portion and a top portion, said method comprising adding at least one air flow channel to the bottom portion of the frame so that the air flow channel directs air toward the lens during use in an amount sufficient to reduce fogging, preferably in an amount sufficient to substantially eliminate fogging. Simultaneously this air flow channel directing of air substantially reduces or eliminates air flow across the eyes of an individual wearing the goggles, thus providing greater eye comfort while also defogging the lens.

It is to be understood that both the foregoing general description and the following detailed description are exemplary and explanatory only, and are not restrictive of the invention.

BRIEF DESCRIPTION OF THE DRAWINGS

Various objects features and advantageous of the present invention are illustrated in the attached figures wherein.

DETAILED DESCRIPTION OF THE INVENTION

Figure 1:
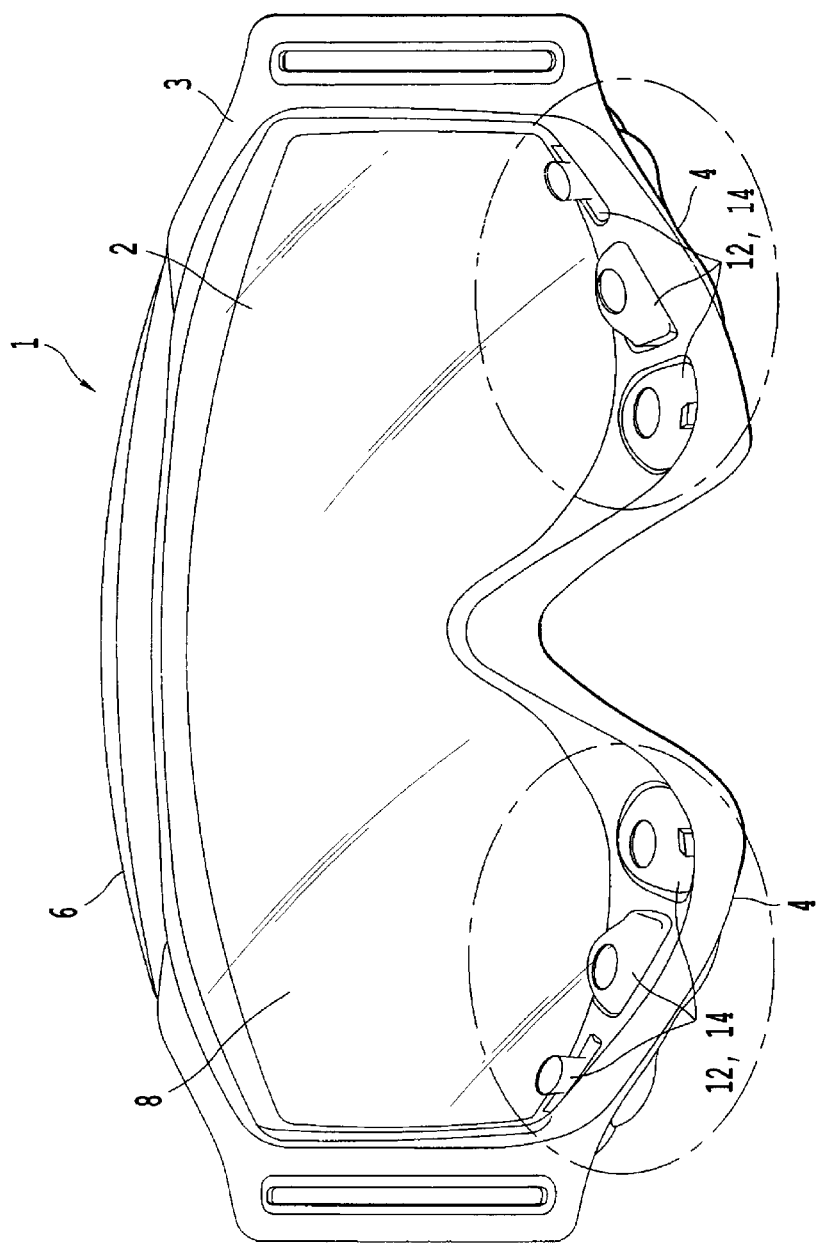
FIG. 1 is a front elevational view of the FOG-RESISTANT GOGGLES of the present invention.
Figure 2:
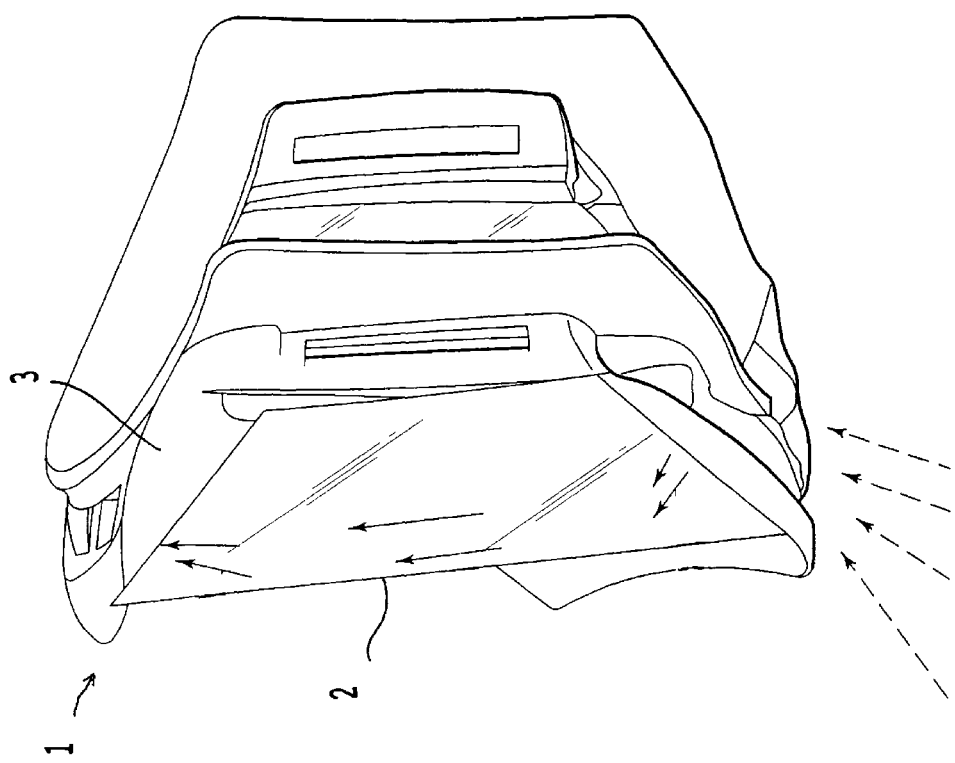
FIG. 2 is a left side elevational view thereof.
Figure 3:
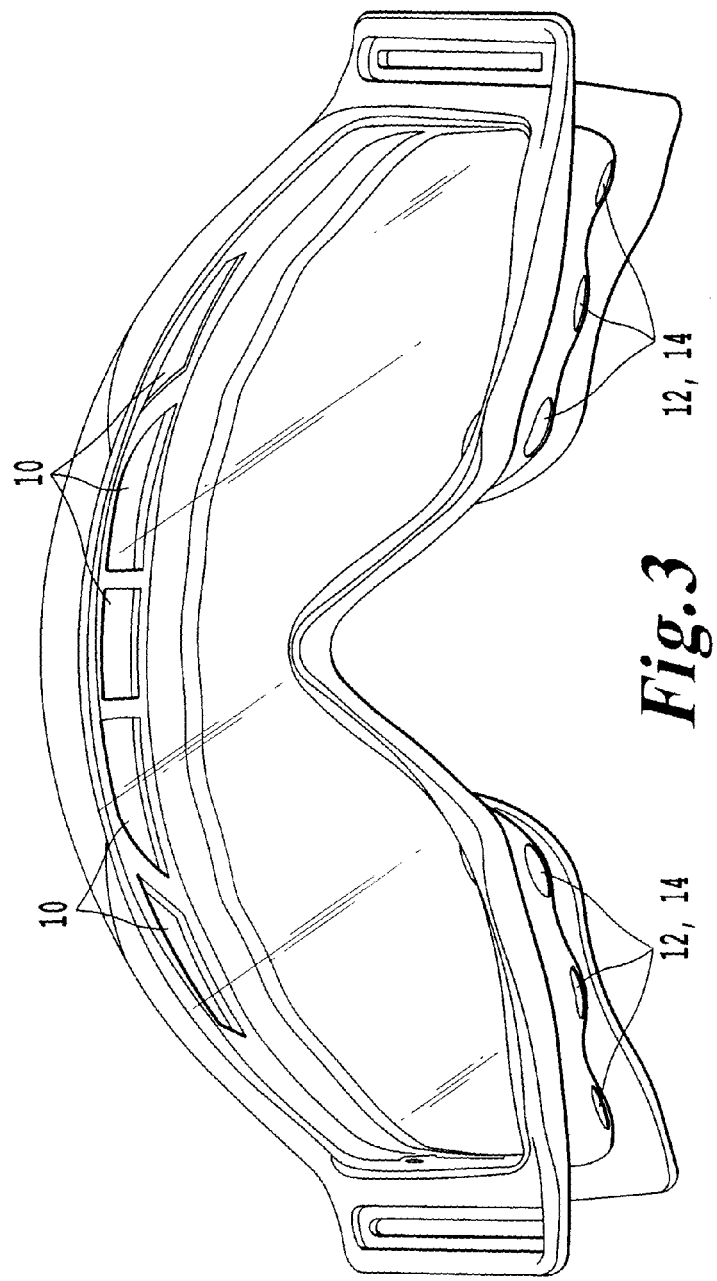
FIG. 3 is a lower front elevational view thereof.
Figure 4:
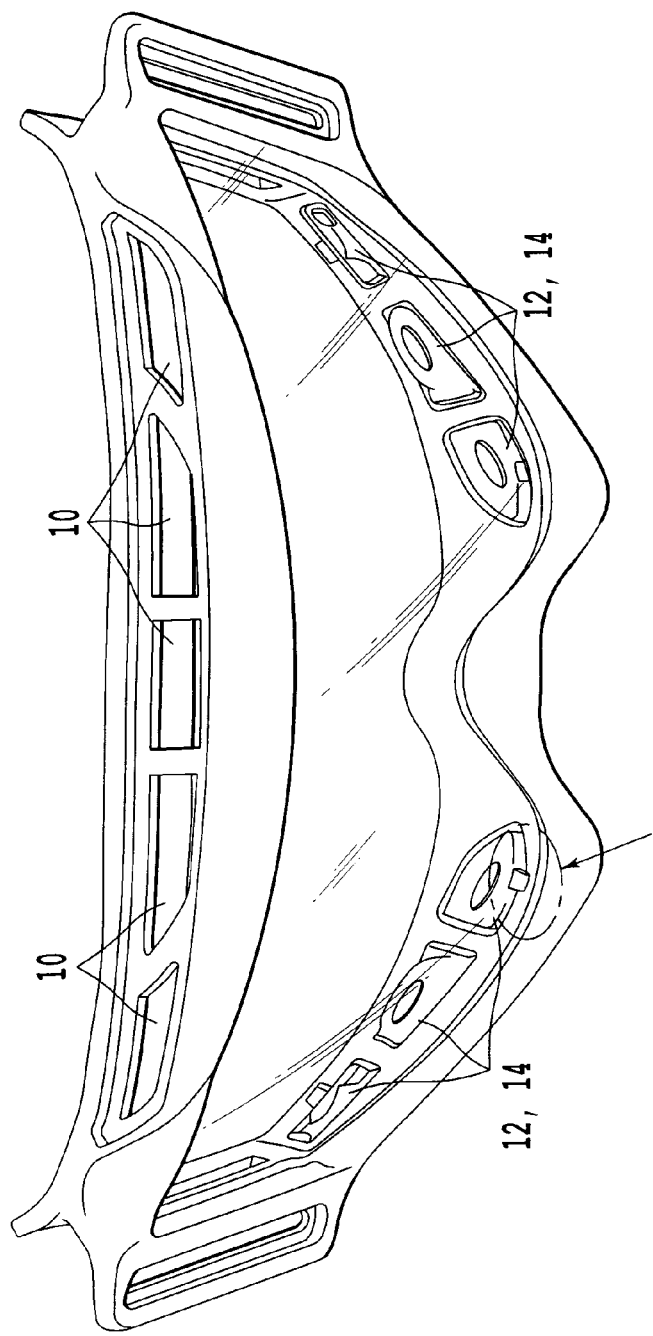
FIG. 4 is a top and front view thereof.
Figure 5:
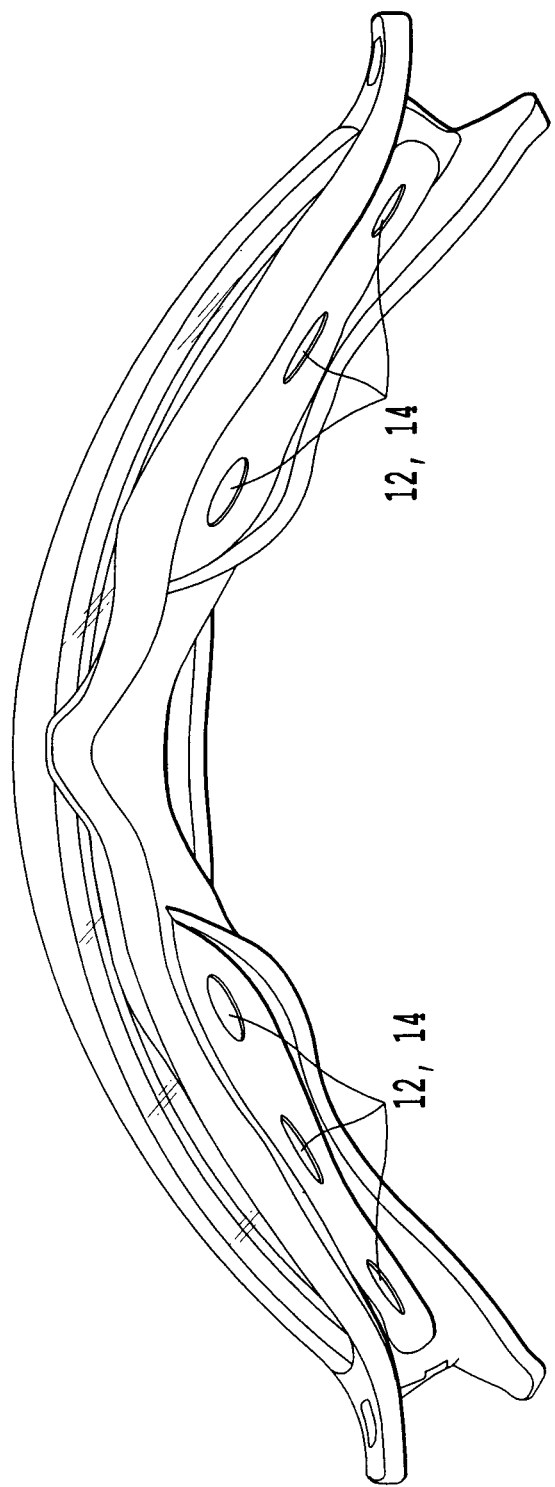
FIG. 5 is a bottom plan view thereof.

As used herein, the expression "at least one" means one or more and thus includes individual components as well as mixtures/combinations.

The compositions and methods of the present invention can comprise, consist of, or consist essentially of the essential elements and limitations of the invention described herein, as well as any additional or optional ingredients, components, or limitations described herein or any otherwise useful ingredient or component found in eyewear.

According to one embodiment of the present invention, goggles comprising at least one lens encompassed within a frame comprising a bottom portion and a top portion, wherein the top portion of the frame comprises at least one vent and wherein the bottom portion of the frame comprises at least one air flow channel which directs air toward the lens during use in an amount sufficient to reduce fogging are provided. These goggles can be used for any purpose. Preferably, the goggles are used for sports-related activities such as, for example, skiing (downhill or cross-country), skating (particularly speed skating), sky-diving, snowboarding, ski-jumping, motorcycling, etc.

In accordance with preferred embodiments, the goggles 1 comprise at least one lens 2. Typically, the number of lenses present will depend upon the structure of the goggles frame. Preferably, the frame structure 3 accommodates a single lens. However, it is possible that the frame structure 3 could accommodate two or more lenses. For example, the frame structure could possess a structural element running parallel to the bridge of the user's nose which divides the user's viewing area approximately in half. One side of such a structure could contain a first lens. The other side of such a structure could contain a second lens. Such a bifurcated structure could be useful, for example, if the lenses were prescription lenses and the user's eyes needed different prescriptions.

According to preferred embodiments, the at least one lens 2 comprises or is made of see-through material: that is, material which the user can see through without difficultly. The at least one lens can be clear, tinted, coated, provide UV protection (protection from ultra-violet rays), or modified in any other way in which eyewear lenses can be modified. Suitable materials for such lens(es) include, but are not limited to, any material capable of being used as a lens in eyewear such as glasses, sunglasses or goggles. Preferably, the at least one lens comprises or is made of a hard plastic material.

According to the present invention, the frame 3 comprises a bottom portion 4 and a top portion 6. The "bottom portion" 4 of the frame 3 is the section below the horizontal median line of the frame. Similarly, the "top portion" 6 of the frame 3 is the section above the horizontal median line of the frame. As also readily understood, "top" and "bottom" portions of the goggles are those portions as defined when the goggles are worn by an individual with the bottom portion being located below eye level of the individual and the top potion being located above eye level. The at least one lens 2 is encompassed within the frame and preferably the at least one lens is completely surrounded by the frame. Together, the frame and the at least one lens define the inner goggle space 8 (that is, the area between the face and the lens encompassed within the frame). According to preferred embodiments, the top portion 6 of the frame 3 comprises at least one vent 10 through which air exits when leaving the inner goggle space.

In accordance with the present invention, the bottom portion of the frame comprises at least one air flow channel 12 which directs air toward the lens during use in an amount sufficient to reduce fogging (that is, in an amount sufficient to reduce condensation on the lens). The bottom portion 4 of the frame 3 can contain one or multiple air flow channels 12 (for example, two, three, four, five, ten, twenty, etc.). Moreover, the air flow channel(s) 12 can be of any size or shape (for example, square, round, rectangular, etc.). Of course, to ensure that sufficient air is directed toward the lens during use, the number of air flow channels 12 may depend upon the size and shape of the air flow channels. For example, the larger the air channels are, the fewer air channels would probably be necessary to achieve the desired amount of airflow. Likewise, the smaller the air channels, the more air channels would probably be necessary. According to particularly preferred embodiments, the at least one air flow channel 12 directs air toward the lens 2 during use in an amount sufficient to substantially eliminate fogging (that is, in an amount sufficient to reduce condensation on the lens such that no visible condensation exists).

According to the present invention, the airflow from the at least one airflow channel 12 travels primarily along the lens 2 (and away from the user's eyes) until it reaches the at least one vent 10 in the top of the frame where the airflow exits the inner goggle space 8. In a particularly preferred embodiment, substantially all airflow entering the inner goggle space 8 is directed toward the lens 2 by airflow channels. By directing the airflow toward the lens, airflow across the eyes of an individual wearing the goggles is substantially reduced or is avoided. This permits greater comfort to the individual while effectively defogging lens of the goggles.

According to preferred embodiments, the airflow is directed to the lens by the air flow channel at an angle between about 5° and about 50°, more preferably from about 10° to about 45°, where the angle is measured between the face of the lens and the airflow from the air flow channels. Of course, the individual air flow channels may direct air toward the lens at the same or different angles.

It is to be understood that reversing the airflow by relocating the airflow channel(s) to the top portion of the frame and the vent(s) to the bottom portion of the frame is also possible as long as such reversal, in accordance with the present invention, provides airflow to the lens in an amount sufficient to reduce fogging, preferably in an amount sufficient to substantially eliminate fogging. Such an embodiment would require a scoop or some other type of attachment to the top portion of the goggle to redirect air so that it travels from the top of the frame to the bottom of the frame.

According to one embodiment of the present invention, the air flow channels 12 are integrally incorporated into the bottom portion 4 of the frame 3. That is, the air flow channels 12 are part of the frame structure. In accordance with this embodiment, the air flow channels are preferably produced concurrently with the bottom portion 4 of the frame. For example, the mold which is used to produce the bottom portion of the frame comprises the necessary elements to allow the air flow channels to be produced at the same time the bottom portion of the frame is produced. Alternatively, the air flow channels can be produced at a later time. For example, the air flow channels can be added to a previously-produced bottom portion of a frame by, for example, drilling through the bottom portion 4 of the frame 3 to create an air flow channel.

According to another embodiment, the air flow channels are not integrally incorporated into the bottom portion 4 of the frame. According to this embodiment, the air flow channels are preferably added to a previously-produced bottom portion of a frame by adding at least one air flow insert 14 comprising at least one air flow channel 12 to the bottom portion 4 of the frame. The bottom portion of the frame can contain one or multiple air flow inserts 14 (for example, two, three, four, five, ten, twenty, etc.), each of which individually can contain one or multiple air flow channels inserts 14 (for example, two, three, four, five, ten, twenty, etc.). Moreover, the air flow insert(s) can be of any size or shape (for example, square, round, rectangular, etc.). Such air flow inserts would be particularly useful for retrofitting existing goggles with the air flow channels of the present invention to allow previously-produced goggles the defogging and safety benefits afforded by the present invention.

According to preferred embodiments, the goggles of the present invention further comprise means for maintaining the goggles in place during use. Any suitable means could be used to maintain the goggles in place during use such as, for example, attaching an elastic strap to the goggles, incorporating the goggles into a helmet, suction, adhesives, etc.

According to other embodiments of the present invention, molds for producing goggles comprising at least one lens 2 encompassed within a frame comprising a bottom portion and a top portion, wherein the top portion of the frame comprises at least one vent 10 and wherein the bottom portion 4 of the frame 3 comprises at least one air flow channel 12 which directs air toward the lens during use in an amount sufficient to reduce fogging are provided. That is, molds for producing the goggles of the present invention are provided. Preferably, such molds can be used in injection molding processes to allow the goggles of the present invention to be made through known injection molding techniques.

According to yet other embodiments of the present invention, processes for producing goggles comprising at least one lens 2 encompassed within a frame 3 comprising a bottom portion 4 and a top portion 6, wherein the top portion 6 of the frame comprises at least one vent 10 and wherein the bottom portion 4 of the frame comprises at least one air flow channel 12 which directs air toward the lens during use in an amount sufficient to reduce fogging comprising using a mold for such goggles are provided. Preferably, such processes are injection molding processes.

According to still other embodiments of the present invention, methods for defogging goggles during use comprising directing air toward the lens in an amount sufficient to reduce fogging are provided. Preferably, the amount of air directed toward the lens is sufficient to substantially eliminate fogging.

According to yet other embodiments of the present invention, methods for producing goggles comprising at least one lens encompassed within a frame comprising a bottom portion and a top portion, the method comprising adding at least one air flow insert comprising at least one air flow channel to the bottom portion of the frame so that the air flow channel directs air toward the lens during use in an amount sufficient to reduce fogging, are provided.

According to still other embodiments of the present invention, methods for producing goggles comprising at least one lens encompassed within a frame comprising a bottom portion and a top portion, the method comprising adding at least one air flow channel to the bottom portion of the frame so that the air flow channel directs air toward the lens during use in an amount sufficient to reduce fogging, are provided.

Unless otherwise indicated, all numbers used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements.

With respect to the above description, it is to be understood that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to falling within the scope of the invention. As an example, edge portions of the frame other than the bottom portion and top portion could be utilized to locate the vent and air flow channel. In this regard, opposite side portions could instead by utilized on the air channel, could patentably be provided in the top portion while the bottom portion has the at least one vent formed therein. As long as air flow is virtually directed toward the lens from the air channel and flow substantially parallel to the lens, a defogging effect could result and these variations are thus within the scope of the claims of the present application. In addition the channel flow and control inserts can be inserted into openings formed in the frame or can be integrally provided as openings in the frame.

What is claimed is:

1. Goggles comprising at least one lens encompassed within and surrounded by a frame comprising a frame bottom portion and top portion which defines an inner goggle space, wherein the top portion of the frame comprises at least one vent through which air exits when leaving the inner goggle space and wherein the bottom portion of the frame comprises at least one air flow channel which directs air toward the lens at an angle between about 5 degrees and about 50 degrees in an amount sufficient to reduce fogging of the lens.

2. The goggles of claim 1, further comprising means for maintaining the goggles in place during use.

3. The goggles of claim 2, wherein the means for maintaining the goggles in place during use comprises an elastic strap.

4. The goggles of claim 1, wherein the at least one lens is completely surrounded by the frame.

5. The goggles of claim 4, further comprising means for maintaining the goggles in place during use.

6. The goggles of claim 5, wherein the means for maintaining the goggles in place during use comprises an elastic strap.

7. The goggles of claim 4, wherein sufficient air is directed toward the lens during use to substantially eliminate fogging.

8. The goggles of claim 4, wherein the at least one air flow channel directs air toward the lens at an angle between about 10 degrees and about 45 degrees.

9. The goggles of claim 4, wherein the at least one air flow channel is integrally incorporated into the bottom portion of the frame.

10. The goggles of claim 4, wherein the bottom portion of the frame comprises at least two air flow channels.

11. The goggles of claim 4, wherein the at least one lens comprises UV protection.

12. The goggles of claim 1, wherein sufficient air is directed toward the lens during use to substantially eliminate fogging.

13. The goggles of claim 1, wherein the at least one air flow channel directs air toward the lens at an angle between about 10 degrees and about 45 degrees.

14. The goggles of claim 1, wherein the at least one air flow channel is integrally incorporated into the bottom portion of the frame.

15. The goggles of claim 1, wherein the bottom portion of the frame comprises at least two air flow channels.

16. The goggles of claim 1, wherein the at least one lens comprises UV protection.

17. The goggles of claim 1, wherein the top portion of the frame does not contain a scoop which redirects air so that it travels from the top of the frame to the bottom of the frame.

18. Goggles, comprising at least one lens encompassed within and surrounded by a frame comprising a frame bottom portion and top portion which defines an inner goggle space, wherein the top portion of the frame comprises at least one vent through which air exits when leaving the inner goggle space and wherein an opposite portion of the frame comprises at least one air flow channel which directs air towards the lens at an angle between about 5 degrees and about 50 degrees and away from an eye portion of an individual wearing the goggles.

* * * * *